United States Patent [19]

Elbe et al.

[11] Patent Number: 4,806,559

[45] Date of Patent: Feb. 21, 1989

[54] NOVEL SUBSTITUTED HYDROXYALKYL-AZOLE ANTIMYCOTIC AGENTS

[75] Inventors: Hans-Ludwig Elbe; Jörg Stetter, both of Wuppertal; Karl H. Büchel, Burscheid; Klaus Schaller, Wuppertal; Manfred Plempel, Haan, all of Fed. Rep. of Germany

[73] Assignee: Bayer Aktiengesellschaft, Leverkusen, Fed. Rep. of Germany

[21] Appl. No.: 757,033

[22] Filed: Jul. 18, 1985

[30] Foreign Application Priority Data

Jul. 27, 1984 [DE] Fed. Rep. of Germany ....... 3427844

[51] Int. Cl.$^4$ .................. A01N 43/64; C07D 249/08
[52] U.S. Cl. .................................. 514/383; 514/399; 548/262; 548/341
[58] Field of Search ......................... 548/262; 514/383

[56] References Cited

U.S. PATENT DOCUMENTS

| | | | |
|---|---|---|---|
| 4,451,281 | 5/1984 | Elbe et al. | 548/341 |
| 4,472,416 | 9/1984 | Stetter et al. | 548/341 |
| 4,507,140 | 3/1985 | Sugavanam | 548/101 |
| 4,584,308 | 4/1986 | Elbe et al. | 514/383 |
| 4,632,932 | 12/1986 | Kramer et al. | 514/383 |

FOREIGN PATENT DOCUMENTS

| | | | |
|---|---|---|---|
| 111234 | 6/1984 | European Pat. Off. | 548/262 |
| 2623129 | 11/1977 | Fed. Rep. of Germany | 548/341 |
| 3237400 | 4/1984 | Fed. Rep. of Germany | 548/262 |

OTHER PUBLICATIONS

J. Am. Chem. Soc. 87, 1363–1364 (1965).
Kutsama et al., Heterocycles 8, 397–401 (1977).

Primary Examiner—Richard L. Raymond
Assistant Examiner—Patricia L. Morris
Attorney, Agent, or Firm—Sprung Horn Kramer & Woods

[57] ABSTRACT

An antimycotic agent, comprising a compound of the formula

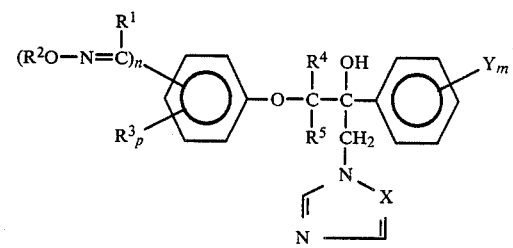

in which
$R^1$ is hydrogen, alkyl, optionally substituted phenyl or optionally substituted benzyl,
$R^2$ is hydrogen, alkyl, alkenyl, alkynyl, optionally substituted phenyl or optionally substituted benzyl,
$R^3$ and Y each independently is halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenoxyalkyl,
$R^4$ and $R^5$ each independently is alkyl,
X is a nitrogen atom or the CH group,
m is 0, 1, 2 or 3,
n is 1 or 2, and
p is 0, 1 or 2,
or an acid addition salt thereof.

13 Claims, No Drawings

NOVEL SUBSTITUTED HYDROXYALKYL-AZOLE ANTIMYCOTIC AGENTS

The present invention relates to new substituted hydroxyalkyl-azoles, a process for their preparation and antimycotic agents containing these compounds.

It has already been disclosed that certain hydroxyalkyl-azolyl derivatives have good antimycotic properties.

New substituted hydroxyalkyl-azoles of the general formula

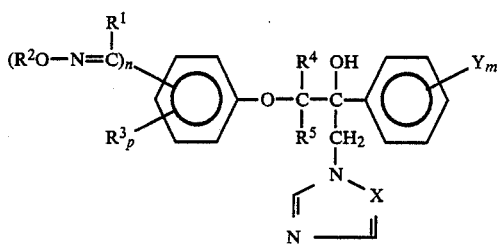

in which
R¹ represents hydrogen, alkyl, optionally substituted phenyl or optionally substituted benzyl,
R² represents hydrogen, alkyl, alkenyl, alkynyl, optionally substituted phenyl or optionally substituted benzyl,
n represents the number 1 or 2,
R³ represents the meanings of Y,
p represents the number 0, 1 or 2,
R⁴ represents alkyl,
R⁵ represents alkyl,
X represents a nitrogen atom or the CH group,
Y represents halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenoxyalkyl and
m represents the number 0, 1, 2 or 3,
and acid addition salts thereof, have been found.

The compounds of the formula (I) have at least one and in some cases two asymmetric carbon atoms and can therefore be obtained in various optical isomer forms.

It has furthermore been found that the substituted hydroxyalkyl-azoles of the formula (I) are obtained by a process in which oxiranes of the formula

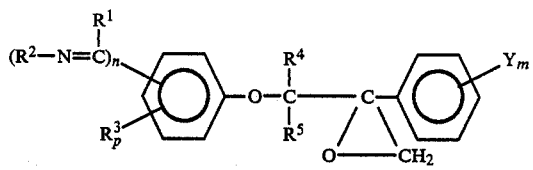

in which R¹, R², R³, R⁴, R⁵, Y and the indices m, n and p have the abovementioned meaning, are reacted with azoles of the formula

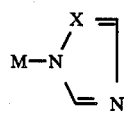

in which
X has the abovementioned meaning and
M represents hydrogen or an alkali metal,
in the presence of a diluent and if appropriate in the presence of a base.

If appropriate, an acid can then be added onto the compounds of the formula (I) thus obtained.

The new substituted hydroxyalkyl-azoles of the formula (I) have powerful antimycotic properties. Surprisingly, the compounds according to the invention exhibit, in particular, a better therapeutically usable in vivo activity than the chemically similar compounds known from the prior art. The substances according to the invention thus represent an enrichment of pharmacy.

The new substituted hydroxyalkylazoles are also interesting intermediates. Thus, for example, the compounds of the general formula (I) can be converted into the corresponding ethers on the hydroxyl group in the customary manner. Furthermore, acyl or carbamoyl derivatives of the compounds of the general formula (I) can be obtained by reaction with, for example, acyl halides or carbamoyl chlorides in a manner which is known in principle.

Formula (I) provides a general definition of the substituted hydroxyalkylazoles according to the invention. Preferably, in this formula,
R¹ represents hydrogen or straight-chain or branched alkyl with 1 to 10 carbon atoms, or represents phenyl or benzyl, each of which is optionally mono-, di- or tri-substituted by identical or different substituents, possible substituents having the meanings of Y;
R² represents hydrogen, straight-chain or branched alkyl with 1 to 10 carbon atoms or straight-chain or branched alkenyl or alkynyl with in each case 3 to 10 carbon atoms, or represents phenyl or benzyl, each of which is optionally mono-, di- or tri-substituted by identical or different substituents, possible substituents having the meanings of Y;
n represents the number 1 or 2;
R³ represents the meanings of Y;
p represents the number 0, 1 or 2;
R⁴ represents straight-chain or branched alkyl with 1 to 4 carbon atoms;
R⁵ represents straight-chain or branched alkyl with 1 to 4 carbon atoms;
X represents a nitrogen atom or the CH group;
Y represents halogen, alkyl with 1 to 4 carbon atoms, cycloalkyl with 5–7 carbon atoms, alkoxy or alkylthio with in each case 1 to 4 carbon atoms or halogenoalkyl, halogenoalkoxy or halogenoalkylthio with in each case 1 or 2 carbon atoms and 1 to 5 identical or different halogen atoms, such as, preferably, fluorine and chlorine atoms, or represents phenyl, phenoxy, phenylalkyl or phenylalkoxy with 1 or 2 carbon atoms in the alkyl part or in the alkoxy part, in each case optionally substituted by halogen and alkyl with 1 or 2 carbon atoms; and
m represents the number 0, 1, 2 or 3.

Particularly preferred compounds of the formula (I) are those in which
R¹ represents hydrogen or straight-chain or branched alkyl with 1 to 4 carbon atoms, or represents phenyl or benzyl, each of which is optionally mono- or di-substituted by identical or different substituents, possible substituents having the meanings of Y;
R² represents hydrogen, straight-chain or branched alkyl with 1 to 4 carbon atoms or straight-chain or branched alkenyl or alkynyl with in each case 3 or 4 carbon atoms, or represents phenyl or benzyl, in each case optionally mono- or di-substituted by identical or different substituents, possible substituents having the meanings of Y;

n represents the number 1 or 2;
$R^3$ represents the meanings of Y;
p represents the number 0, 1 or 2;
$R^4$ represents methyl or ethyl;
$R^5$ represents methyl or ethyl;
X represents a nitrogen atom or the CH group; Y represents fluorine, chlorine, bromine, methyl, isopropyl, tert.-butyl, cyclohexyl, methoxy, methylthio, trifluoromethyl, trifluoromethoxy or trifluoromethylthio, or represents phenyl, phenoxy, benzyl or benzyloxy, in each case optionally substituted by fluorine, chlorine or methyl; and m represents the number 0, 1 or 2.

Addition products of acids and those substituted hydroxyalkyl-azoles of the formula (I) in which the substituents $R^1$, $R^2$, $R^3$, $R^4$, $R^5$, X and Y and the indices m, n and p have the meanings which have already been mentioned as preferred for the substituents and indices are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

The following compounds of the formula (I) may be mentioned specifically, in addition to the compounds mentioned in the preparation Examples (X represents either a nitrogen atom or the CH group):

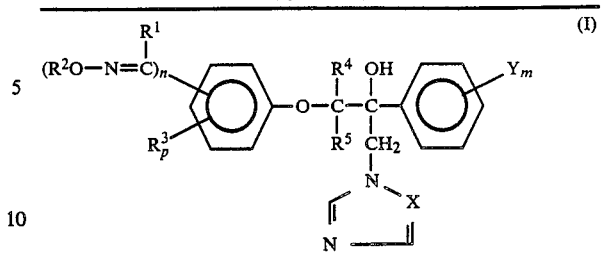

| $(R^2O-N=C-)_n$ | $R^3_p$ | $R^4$ | $R^5$ | $Y_m$ |
|---|---|---|---|---|
| 4-CH₃O—N=CH— | 2-Cl | CH₃ | CH₃ | 2-F |
| 4-CH₃O—N=CH— | 2-F | CH₃ | CH₃ | 2-F |
| 2-CH₃O—N=CH— | — | CH₃ | CH₃ | 2-F |
| 4-CH₃O—N=CH— | — | CH₃ | CH₃ | 2-F |
| 2-CH₃O—N=CH— | 4-Cl | CH₃ | CH₃ | 2-F |
| 2-CH₃O—N—CH— | 4-F | CH₃ | CH₃ | 2-F |
| 4-C₄H₉O—n=CH— | — | CH₃ | CH₃ | 2-F |
| 4-CH₂=CH—CH₂O—N=CH— | — | CH₃ | CH₃ | 2-F |
| 4-HC≡C—CH₂O—N=CH— | — | CH₃ | CH₃ | 2-F |
| 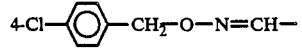 | — | CH₃ | CH₃ | 2-F |

| $(R^2O-N=C-)_n$ | $R^3_p$ | $R^4$ | $R^5$ | $Y_m$ |
|---|---|---|---|---|
| 4-CH₃O—N=C—(4-Cl-phenyl) | — | CH₃ | CH₃ | 2-F |
| 4-CH₃O—N=C(CH₃)— | — | CH₃ | CH₃ | 2-F |
| 2-CH₃O—N=C(CH₃)— | — | CH₃ | CH₃ | 2-F |
| 4-CH₃O—N=CH— | 2-Cl | CH₃ | CH₃ | 4-Cl |
| 4-CH₃O—N=CH— | 2-F | CH₃ | CH₃ | 4-Cl |
| 2-CH₃O—N=CH— | — | CH₃ | CH₃ | 4-Cl |
| 2-CH₃O—N=CH— | 4-Cl | CH₃ | CH₃ | 4-Cl |
| 2-CH₃O—N=CH— | 4-F | CH₃ | CH₃ | 4-Cl |
| 4-C₄H₉O—N=CH— | — | CH₃ | CH₃ | 4-Cl |
| 4-CH₂=CH—CH₂O—N=CH— | — | CH₃ | CH₃ | 4-Cl |
| 4-CH≡C—CH₂O—N=CH— | — | CH₃ | CH₃ | 4-Cl |
| 4-Cl-C₆H₄-CH₂O—N=CH— | — | CH₃ | CH₃ | 4-Cl |
| 4-CH₃O—N=C—(4-Cl-phenyl) | — | CH₃ | CH₃ | 4-Cl |
| 2-CH₃O—N=C(CH₃)— | — | CH₃ | CH₃ | 4-Cl |
| 4-CH₃O—N=CH— | 2-Cl | CH₃ | CH₃ | 2-Cl |
| 4-CH₃O—N=CH— | 2-F | CH₃ | CH₃ | 2-Cl |
| 2-CH₃O—N=C(CH₃)— | — | CH₃ | CH₃ | 2-Cl |
| 2-CH₃O—N=CH— | — | CH₃ | CH₃ | 2-Cl |
| 2-CH₃O—N=CH— | 4-Cl | CH₃ | CH₃ | 2-Cl |
| 2-CH₃O—N=CH— | 4-F | CH₃ | CH₃ | 2-Cl |
| 4-C₄H₉O—N=CH— | — | CH₃ | CH₃ | 2-Cl |
| 4-CH₂=CH—CH₂O—N=CH— | — | CH₃ | CH₃ | 2-Cl |
| 4-CH≡C—CH₂O—N=CH— | — | CH₃ | CH₃ | 2-Cl |
| 4-Cl-C₆H₄-CH₂O—N=CH— | — | CH₃ | CH₃ | 2-Cl |
| 4-CH₃O—N=C—(4-Cl-phenyl) | — | CH₃ | CH₃ | 2-Cl |
| 4-CH₃—O—N=C(CH₃)— | — | CH₃ | CH₃ | 2-Cl |
| 4-CH₃O—N=CH— | 2-Cl | CH₃ | CH₃ | 4-F |
| 4-CH₃O—N=CH— | 2-F | CH₃ | CH₃ | 4-F |
| 2-CH₃O—N=CH— | — | CH₃ | CH₃ | 4-F |
| 2-CH₃O—N=C(CH₃)— | — | CH₃ | CH₃ | 4-F |
| 2-CH₃O—N=CH— | 4-Cl | CH₃ | CH₃ | 4-F |
| 2-CH₃O—N=CH— | 4-F | CH₃ | CH₃ | 4-F |
| 4-C₄H₉O—N=CH— | — | CH₃ | CH₃ | 4-F |
| 4-CH₂=CH—CH₂O—N=CH— | — | CH₃ | CH₃ | 4-F |
| 4-CH≡C—CH₂O—N=CH— | — | CH₃ | CH₃ | 4-F |
| 4-Cl-C₆H₄-CH₂O—N=CH— | — | CH₃ | CH₃ | 4-F |

-continued

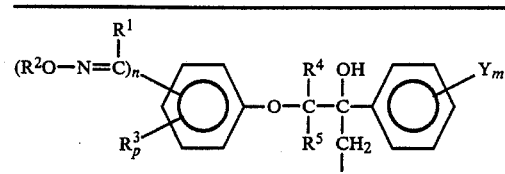

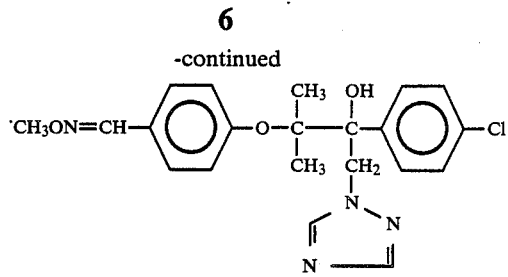

| (R²O—N=C—)ₙ R¹ | R³ₚ | R⁴ | R⁵ | Yₘ |
|---|---|---|---|---|
|  4-CH₃O—N=C— | — | CH₃ | CH₃ | 4-F |
| 4-CH₃O—N=C(CH₃)— | — | CH₃ | CH₃ | 4-F |
| 4-CH₃O—N=CH— | 2-Cl | CH₃ | CH₃ | 2,4-Cl₂ |
| 4-CH₃O—N=CH— | 2-F | CH₃ | CH₃ | 2,4-Cl₂ |
| 2-CH₃O—N=CH— | — | CH₃ | CH₃ | 2,4-Cl₂ |
| 4-CH₃O—N=CH— | — | CH₃ | CH₃ | 2,4-Cl₂ |
| 2-CH₃O—N=CH— | 4-Cl | CH₃ | CH₃ | 2,4-Cl₂ |
| 2-CH₃O—N=CH— | 4-F | CH₃ | CH₃ | 2,4-Cl₂ |
| 4-C₄H₉—N=CH— | — | CH₃ | CH₃ | 2,4-Cl₂ |
| 4-CH₂=CH—CH₂O—N=CH— | — | CH₃ | CH₃ | 2,4-Cl₂ |
| 4-CH≡C—CH₂O—N=CH— | — | CH₃ | CH₃ | 2,4-Cl₂ |
| 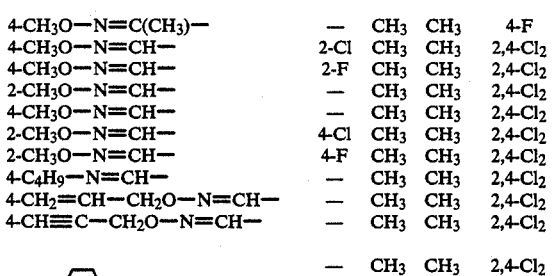 4-Cl—⟨⟩—CH₂O—N=CH— | — | CH₃ | CH₃ | 2,4-Cl₂ |
|  4-CH₃O—N=C— | — | CH₃ | CH₃ | 2,4-Cl₂ |
| 4-CH₃O—N=C(CH₃)— | — | CH₃ | CH₃ | 2,4-Cl₂ |
| 2-CH₃O—N=C(CH₃)— | — | CH₃ | CH₃ | 2,4-Cl₂ |
| 4-CH₃O—N=CH— | — | CH₃ | CH₃ | 3-Cl |
| 4-CH₃O—N=CH— | — | CH₃ | CH₃ | 3-F |
| 4-CH₃O—N=CH— | — | CH₃ | CH₃ | 4-Br |
| 4-CH₃O—N=CH— | — | CH₃ | CH₃ | 2,5-Cl₂ |
| 4-CH₃O—N=CH— | — | CH₃ | CH₃ | 4-CH₃ |
| 4-CH₃O—N=CH— | — | CH₃ | CH₃ | 2-CH₃ |
| 4-CH₃O—N=CH— | — | CH₃ | CH₃ | 4-OCF₃ |
| 4-CH₃O—N=CH— | — | CH₃ | CH₃ | 4-SCF₃ |
| 4-CH₃O—N=CH— | — | CH₃ | CH₃ | 4-CF₃ |

If, for example, 2-(4-chlorophenyl)-2-[2(4-methoxyiminomethylphenoxy)-prop-2-yl]-oxirane and 1,2,4-triazole are used as starting substances, the course of the process according to the invention can be represented by the following equation:

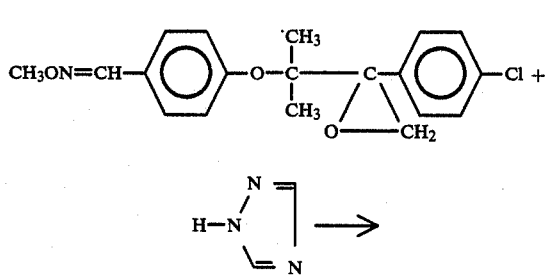

Formula (II) provides a general definition of the oxiranes to be used as starting substances for carrying out the process according to the invention. In this formula, $R^1$, $R^2$, $R^3$, $R^4$, $R^5$ and Y and the indices m, n and p preferably have the meanings which have already been mentioned as preferred for these substituents and indices in connection with the description of the substances of the formula (I) according to the invention.

The oxiranes of the formula (II) are not yet known. However, they can be obtained in a generally known manner by a process in which ketones of the formula

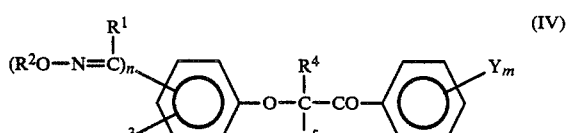

in which $R^1$, $R^2$, $R^3$, $R^4$, $R^5$, Y and the indices m, n and p have the abovementioned meaning, either
(α) are reacted with dimethylsulphonium methylide of the formula

in the presence of a diluent, or (β) are reacted with trimethylsulphonium methyl sulphate of the formula

in the presence of an inert organic solvent and in the presence of a base.

The dimethyloxosulphonium methylide of the formula (V) required in process variant (α) is known (compare J. Am. Chem. Soc. 87, 1363–1364 (1965)). In the above reaction, it is processed in the freshly prepared state, in that it is produced in situ by reaction of trimethyloxosulphonium iodide with sodium hydride or sodium amide in the presence of a diluent.

The trimethylsulphonium methyl sulphate of the formula (VI) required in process variant (β) is likewise known (cf. Heterocycles 8, 397 (1977)). In the above reaction, it is likewise employed in the freshly prepared state, in that it is produced in situ by reaction of dimethyl sulphide with dimethyl sulphate.

The preferred possible diluent in variant (α) of the process for the preparation of the oxiranes of the formula (II) is dimethyl sulphoxide.

The reaction temperatures can be varied within a substantial range in process variant (α) described above. In general, the reaction is carried out at temperatures between 20° C. and 80° C.

The process for the preparation of the oxiranes of the formula (II) by variant (α) is carried out and the reaction mixture obtained in this synthesis is worked up by customary methods (cf. J. Am. Chem. Soc. 87, 1363-1364 (1965)).

The preferred possible inert organic solvent in variant (β) for the preparation of the oxiranes of the formula (II) is acetonitrile.

Bases which can be used in process variant (β) are strong inorganic or organic bases. The preferred possible base is sodium methylate.

The reaction temperatures can be varied within a certain range in process variant (β) described above. In general, the reaction is carried out at temperatures between 0° C. and 60° C., preferably at room temperature.

The process for the preparation of the oxiranes of the formula (II) by variant (β) is carried out and the reaction product obtained in this synthesis is worked up by customary methods (cf. Heterocycles 8, 397 (1977)).

If appropriate, the oxiranes of the formula (II) can be further reacted directly without isolation in the process according to the invention.

The ketones of the formula (IV) required as starting substances in the preparation of the oxiranes of the formula (II) are obtained by a process in which corresponding halogenoketones of the formula

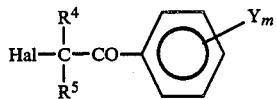

in which

R⁴, R⁵, Y and the index n have the abovementioned meaning and

Hal represents halogen, preferably chlorine or bromine, are heated with phenols of the formula

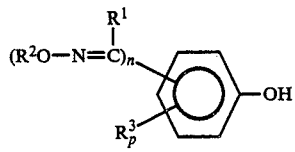

in which R¹, R², R³ and the indices n and p have the abovementioned meaning, in the presence of an inert organic solvent, such as, for example, toluene, and in the presence of an acid-binding agent, such as, for example, potassium carbonate, at temperatures between 80° and 120° C. (cf. also the preparation examples).

The halogenoketones of the formula (VII) and the phenols of the formula (VIII) are known or can be obtained in a known manner.

Formula (III) provides a general definition of the azoles also to be used as starting substances for the process according to the invention. In this formula, X preferably has the meanings which have already been mentioned as preferred for this substituent in the definition of the invention. M preferably represents hydrogen, sodium or potassium.

Possible diluents for the process according to the invention are organic solvents which are inert under the reaction conditions. Preferred solvents include alcohols, such as, for example, ethanol, methoxyethanol or propanol; ketones, such as, for example, 2-butanone; nitriles, such as, for example, acetonitrile; esters, Such as ethyl acetate; ethers, such as, for example, dioxane; aromatic hydrocarbons, such as, for example, benzene and toluene; or amides, such as, for example, dimethylformamide.

Possible bases for the reaction according to the invention are all the inorganic and organic bases which can usually be employed. Preferred bases include alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the process according to the invention. In general, the reaction is carried out at temperatures between 0° and 200° C., preferably between 60° and 150° C.

In carrying out the process according to the invention, 1 to 2 moles of azole of the formula (III) and, if appropriate, 1 to 2 moles of base are preferably employed per mole of oxirane of the formula (II); the end produces are isolated in the generally customary manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The compounds of the formula (I) which can be used according to the invention, their ester derivatives and their acid addition salts display antimicrobial actions, in particular powerful antimycotic actions. They possess a very broad antimycotic action spectrum, especially against dermatophytes and blastomycetes as well as biphase fungi, for example against species of Candida, such as *Candida albicans*, species of Epidermophyton, such as *Epidermophyton floccosum*, species of Aspergillus, such as *Aspergillus niger* and *Aspergillus fumigatus*, species of Trichophyton, such as *Trichophyton mentagrophytes*, species of Microsporon, such as *Microsporon felineum*, and species of Torulospsis, such as *Torulospsis glabrata*. The listing of these microorganisms in no way implies a limitation of the germs which can be combated, but is only of illustrative character.

Examples which may be mentioned of examples of indication in human medicine are: dermatomycoses and systemic mycoses caused by *Trichophyton mentagrophytes* and other species of Trichophyton, species of Microsporon, *Epidermophyton floccosum*, blastomycetes and biphase fungi, as well as moulds.

Examples which may be mentioned of field of indication in veterinary medicine are: all dermatomycoses and systemic mycoses, in particular those caused by the abovementioned pathogens.

The present invention includes pharmaceutical formulations which, in addition to non-toxic, inert pharmaceutically suitable excipients, contain one or more active compounds according to the invention or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half or one third or one quarter of a daily dose.

By non-toxic, inert pharmaceutically suitable excipients there are to be understood solid, semi-solid or liquid diluents, fillers and formulation auxiliaries of very kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, clucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol and glycerol monostearate, (h) absorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, if appropriate in a delayed manner, examples of embedding compositions which can be used being polymeric substances and waxes.

The active compound or compounds, if appropriate with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silocones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders, or mixtures of these substances. Sprays can additionally contain the customary propellants, for example chlorofluorohydrocarbons.

Solutions and emulsions can contain, in addition to the active compound or compounds, the customary excipients, such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propyl alcohol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain colorants, preservatives and additives which improve the odor and flavor for example peppermint oil and eucalyptus oil, and sweeteners, for example saccharin.

The therapeutically active compounds should preferably be present in the pharmaceutical formulations in a concentration of about 0.1 to 99.5%, preferably 0.5 to 95% by weight of the total mixture.

The pharmaceutical formulations can also contain other pharmaceutical active compounds in addition to the active compounds according to the invention.

The pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in human and veterinary medicine for the prevention, alleviation and/or cure of the abovementioned diseases.

The active compounds or the pharmaceutical formulations can be administered locally, orally, parenterally, intraperitoneally and/or rectally, preferably parenterally, in particular intravenously.

In general, it has proved advantageous both in human medicine and in veterinary medicine to administer the active compound of compounds according to the invention in total amounts of about 2.5 to about 200, preferably 5 to 150 mg/kg of body weight every 24 hours, optionally in the form of several individual administrations, in order to achieve the desired results.

In the case of oral administration, the active compounds according to the invention are administered in total amounts of about 2.5 to about 200, preferably 5 to 150 mg/kg of body weight every 24 hours, and in the case of parenteral administration they are administered in total amounts of about 2.5 to about 50, preferably 1 to 25 mg/kg of body weight every 24 hours.

However, it may be necessary to deviate from the dosages mentioned, and in particular to do so as a function of the species and body weight of the subject to be treated, the nature and severity of the disease, the nature of the formulation and of the administration of the medicament and the period or interval over which the administration takes place. Thus it can suffice in some cases to manage with less than the abovementioned amount of active compound, while in other cases the abovementioned amount of active compound must be exceeded. The particular optimum dosage required and

PREPARATION EXAMPLES

Example 1

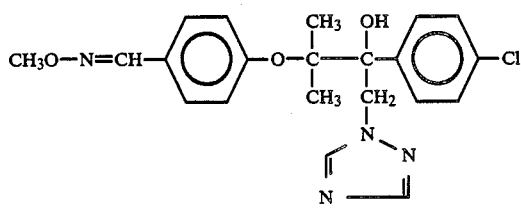

52.8 g (0.153 mole) of 2-(4-chlorophenyl)-2-[2-(4-methoximinomethylphenoxy)-prop-2-yl]-oxirane in 60 ml of n-propanol are added dropwise to a solution of 12.2 g (0.176 mole) of 1,2,4-triazole and 0.35 g (0.0153 mole) of sodium in 100 ml of n-propanol at 90° C. The reaction mixture is subsequently stirred at 90° C. for 20 hours, cooled and concentrated in vacuo. The residue is purified by column chromatography (silica gel; ethyl acetate/cyclohexane=3/1). 10.3 g (16.3% of theory) of 2-(4-chlorophenyl)-3-(4-methoximino-methylphenoxy)-3-methyl-1-(1,2,4-triazol-1-yl)-2-butanol of melting point 54° C. are obtained.

Preparation of the starting substance

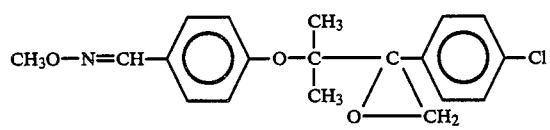

A solution of 40.8 g (0.320 mole) of dimethyl sulphate and 21.8 g (0.355 mole) of dimethyl sulphide in 190 ml of acetonitrile is stirred at room temperature for 5 days. 59.9 g (0.181 mole) of 4-chlorophenyl 2-(4-methoximino-methyl-phenoxy)-2-propyl ketone and 19.7 g of sodium methylate are then added and the reaction mixture is subsequently stirred at room temperature for 20 hours and then concentrated by distillation in vacuo. The residue is stirred with a mixture of 140 ml of ethyl acetate and 110 ml of water.

The ogranic phase is separated off, dried over sodium sulphate and concentrated in vacuo. 52.8 g (84.6% of theory) of crude 2-(4-chlorophenyl)-2-[2-(4-methoximino-methyl-phenoxy)-prop-2-yl]-oxirane are obtained as a viscous oil, which is further reacted directly, without purification.

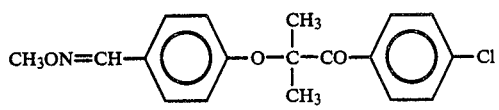

50 g (0.331 mole) of 4-methoximino-methyl-phenol and 45.7 g (0.331 mole) of potassium carbonate in 200 ml of toluene are heated under reflux for 1 hour using a water separator. The mixture is cooled to about 40° C. and 69.8 g of 2-bromo-prop-2-yl 4-chlorophenyl ketone are added dropwise. This reaction mixture is subsequently stirred at 100° C. for 5 hours and is then filtered over a suction filter. The filtrate is washed three times with 10% strength sodium hydroxide solution, rinsed with water, dried over sodium sulphate and concentrated in vacuo. 59.9 g of crude (67.7% of theory) 4-chlorophenyl 2-(4-methoximino-methyl-phenoxy)-2-propyl ketone are obtained as a dark oil, which is reacted directly, without purification.

The following compounds of the general formula

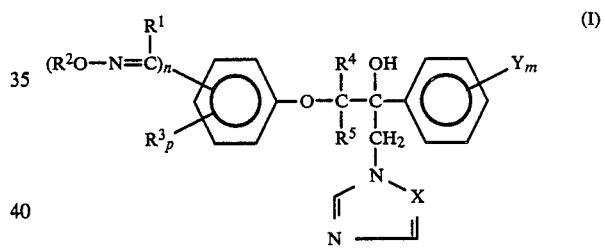

are obtained in a corresponding manner and by the process according to the invention:

| Example No. | (R²O—N=C)ₙ / R³ₚ | R⁴ | R⁵ | X | Yₘ | Melting point (°C.) or $n_D^{20}$ |
|---|---|---|---|---|---|---|
| 2 | CH₃O—N=C(CH₃)— phenyl | CH₃ | CH₃ | N | 4-Cl | 52 |
| 3 | CH₃O—N=CH— phenyl | CH₃ | CH₃ | N | 4-F | 35 |
| 4 | CH₃O—N=CH— phenyl | CH₃ | CH₃ | N | 2-Cl | |

-continued

| Example No. | $(R^2O-N=C)_n$ ... $R^3_p$ (phenyl) | R⁴ | R⁵ | X | $Y_m$ | Melting point (°C.) or $n_D^{20}$ |
|---|---|---|---|---|---|---|
| 5 | $C_3H_7O-N=CH-$ (phenyl) | CH₃ | CH₃ | N | 4-Cl | Oil |

Use Examples

The compounds shown below are employed as comparison substances in the example which follows:

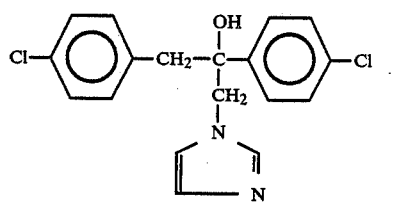

(A)

(see DE-OS (German published specification) No. 2,623,129)

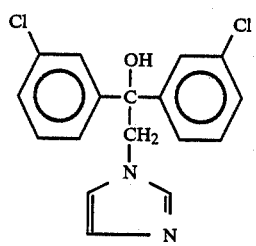

(B)

(see DE-OS (German published specification) No. 2,623,129)

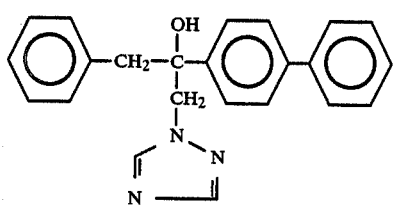

(C)

(see U.S. application Ser. No. 92,805, filed Nov. 9, 1979, now U.S. Pat. No. 4,381,306, corresponding to DE-OS (German specification) No. 2,851,086)

EXAMPLE A

Antimycotic in vivo activity (oral) against candidosis of mice

Description of the experiment:

Mice of the SPF-CF₁ type were infected intravenously with $1-2 \times 10^6$ logarithmically growing Candida cells suspended in physiological saline solution. The animals were treated orally with in each case 25–100 mg of the products/kg of body weight one hour before and seven hours after the infection.

Result:

Untreated animals died 3 to 6 days after infection.

The survival rate on the 6th day after infection was about 5% in the untreated control animals.

In this test, for example, compounds 1 and 2 according to the invention exhibit a better action than the compounds (A), (B) and (C) known from the prior art.

Explanation of symbols:

| | | | |
|---|---|---|---|
| +++++ | = very good action | = | 90% of survivors on the 6th day after infection |
| ++++ | = good action | = | 80% of survivors on the 6th day after infection |
| +++ | = action | = | 60% of survivors on the 6th day after infection |
| ++ | = weak action | = | 40% of survivors on the 6th day after infection |
| + | = trace of action | = | |
| n.a. | = no action | | |

TABLE A

Antimycotic in vivo activity (oral) against candidosis of mice

| Active compound | Action |
|---|---|
| (A) (known) | + |
| (B) (known) | n.a. |
| (C) (known) | n.a. |
| Compounds according to Preparation Example | |
| 1 | ++++ |
| 2 | ++++ |

Example B/Formulations (1.) Solution:

| | |
|---|---|
| Active compound according to formula (I): | 10 g |
| Alcohol, pure (96% strength) | 300 g |
| Isopropyl myristate | 526 g |
| | 836 g |

(2.) Cream:

| | |
|---|---|
| Active compound according to formula (I): | 10 g |
| Aralcel 60 (sorbitan monostearate) | 20 g |
| Tween 60 (polyoxyethylene 20 sorbitan monostearate) | 15 g |
| Spermaceti, synthetic (mixture of esters of saturated C₁₄–C₁₈ fatty acids and C₁₄–C₁₈ fatty alcohols) | 30 g |
| Lanette O (mixture of cetyl alcohol and stearyl alcohol) | 100 g |
| Entanol G (2-octyl-dodecanol) | 135 g |
| Benzyl alcohol | 10 g |
| Water, demineralized | 680 g |
| | 1,000 g |

It will be understood that the specification and examples are illustrative but not limitative of the present invention and that other embodiments within the spirit and scope of the invention will suggest themselves to those skilled in the art.

What is claimed is:
1. A substituted hydroxy-alkylazole of the formula

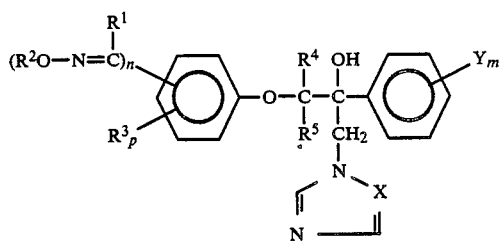

in which
R¹ is hydrogen or alkyl with 1 to 10 carbon atoms, or is phenyl or benzyl each of which is optionally substituted by $Y_m$,
R² is hydrogen or alkyl with 1 to 10 carbon atoms or alkenyl or alkynyl with in each case 3 to 10 carbon atoms, or represents phenyl or benzyl each of which is optionally substituted by $Y_m$,
R³ and Y each independently is halogen, alkyl with 1 to 4 carbon atoms, cycloalkyl with 5–7 carbon atoms, alkoxy or alkylthio with in each case 1 to 4 carbon atoms or halogenoalkyl, halogenoalkoxy or halogenoalkylthio with in each case 1 or 2 carbon atoms and 1 to 5 identical or different halogen atoms; and
R⁴ and R⁵ each independently is alkyl with 1 to 4 carbon atoms,
X is a nitrogen atom,
m is 0, 1, 2 or 3,
n is 1 or 2, and
p is 0, 1 or 2,
or a pharmaceutically acceptable acid addition salt thereof.

2. A substituted hydroxyalkyl-azole or salt according to claim 1, in which
R¹ is hydrogen, alkyl with 1 to 4 carbon atoms, or phenyl or benzyl each of which is substituted by $Y_m$;
R² is hydrogen, alkyl with 1 to 4 carbon atoms, alkenyl or alkynyl with in each case 3 to 4 carbon atoms, or phenyl or benzyl in each case optionally mono- or di-substituted by $Y_m$;
R³ and Y each independently is fluorine, chlorine, bromine, methyl, isopropyl, tert.-butyl, cyclohexyl, methoxy, methylthio, trifluoromethyl, trifluoromethoxy or trifluoromethylthio;
R⁴ and R⁵ each independently is methyl or ethyl, and
m is 0, 1 or 2.

3. A compound according to claim 1, wherein such compound is 2-(4-chlorophenyl)-3-(4-methoximinomethyl-phenoxy)-3-methyl-1-(1,2,4-triazol-1-yl)-2-butanol of the formula

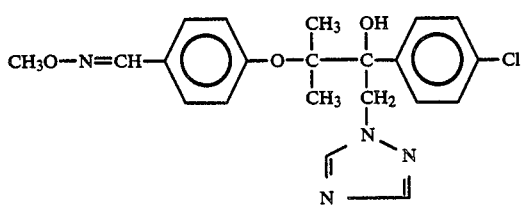

or an acid addition salt thereof.

4. A compound according to claim 1, wherein such compound is 2-(4-chlorophenyl)-3-[4-(1-methoximinoethyl)-phenoxy]-3-methyl-1-(1,2,4-triazol-1-yl)-2-butanol of the formula

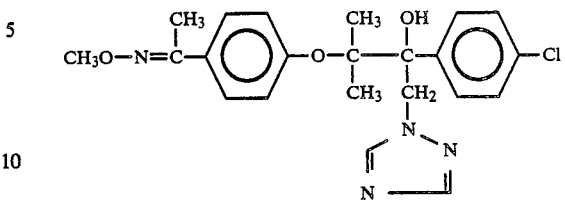

or an acid addition salt thereof.

5. A compound according to claim 1, wherein such compound is 2-(4-fluorophenyl)-3-(4-methoximinomethyl-phenoxy)-3-methyl-1-(1,2,4-triazol-1-yl)-2-butanol of the formula

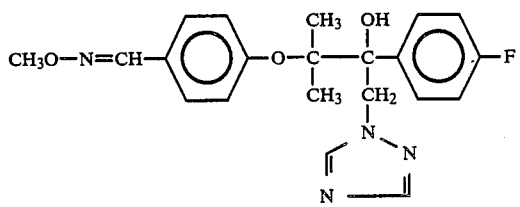

or an acid addition salt thereof.

6. A compound according to claim 1, wherein such compound is 2-(2-chlorophenyl)-3-(4-methoximinomethyl-phenoxy)-3-methyl-1-(1,2,4-triazol-1-yl)-2-butanol of the formula

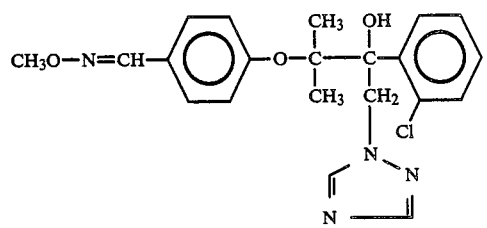

or an acid addition salt thereof.

7. A compound according to claim 1, wherein such compound is 2-(4-chlorophenyl)-3-(4-propoximinomethyl-phenoxy)-3-methyl-1-(1,2,4-triazol-1-yl)-2-butanol of the formula

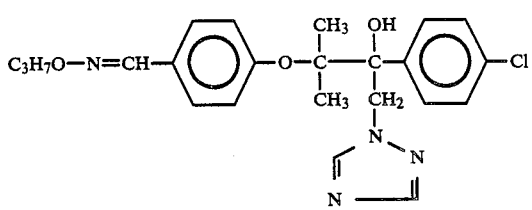

or an acid addition salt thereof.

8. An antimycotic composition comprising a fungicidally effective amount of a compound or salt according to claim 1 in admixture with a pharmaceutically inert diluent.

9. A unit dose of a compound according to claim 8 in the form of a tablet, capsule or ampule.

10. A method of combating fungi which comprises applying to such fungi or a habitat thereof an antimycotically effective amount of a compound or salt according to claim 1.

11. The method according to claim 10, wherein such fungi is a mycosis and the compound or salt is applied to an animal patient.

12. The method according to claim 10, wherein such compound is 2-(4-chlorophenyl)-3-(4-methoximino-methyl-phenoxy)-3-methyl-1-(1,2,4-triazol-1-yl)-2-butanol, 2-(4-chlorophenyl)-3-[4-(1-methoximino-ethyl)-phenoxy]-3-methyl-1-(1,2,4-triazol-1-yl)-2-butanol, 2-(4-fluorophenyl)-3-(4-methoximino-methyl-phenoxy)-3-methyl-1-(1,2,4-triazol-1-yl)-2-butanol, 2-(2-chlorophenyl)-3-(4-methoximino-methyl-phenoxy)-3-methyl-1-(1,2,4-triazol-1-yl)-2-butanol, or 2-(4-chlorophenyl)-3-(4-propoximino-methyl-phenoxy)-3-methyl-1-(1,2,4-triazol-1-yl)-2-butanol, or an acid addition salt thereof.

13. A substituted hydroxyalkyl-azole according to claim 1, wherein p=0.

* * * * *